United States Patent
Chiao et al.

(10) Patent No.: US 9,872,874 B2
(45) Date of Patent: Jan. 23, 2018

(54) DOSAGE REGIMEN FOR SAPACITABINE AND SELICICLIB

(71) Applicant: Cyclacel Limited, London (GB)

(72) Inventors: Judy H. Chiao, Berkeley Heights, NJ (US); David Blake, Angus (GB); Daniella Zheleva, Dundee (GB); Susan Davis, Dundee (GB); Simon Green, Harlow Essex (GB); Geoffrey Shapiro, Boston, MA (US)

(73) Assignee: Cyclacel Limited, London (GB)

( * ) Notice: Subject to any disclaimer, the term of this patent is extended or adjusted under 35 U.S.C. 154(b) by 0 days.

(21) Appl. No.: 14/401,357

(22) PCT Filed: May 14, 2013

(86) PCT No.: PCT/GB2013/051236
§ 371 (c)(1),
(2) Date: Nov. 14, 2014

(87) PCT Pub. No.: WO2013/171473
PCT Pub. Date: Nov. 21, 2013

(65) Prior Publication Data
US 2015/0164933 A1    Jun. 18, 2015

(30) Foreign Application Priority Data

May 15, 2012 (GB) .................................. 1208536.1
Mar. 14, 2013 (GB) .................................. 1304599.2

(51) Int. Cl.
| | | |
|---|---|---|
| *A61K 31/7068* | (2006.01) | |
| *A61K 31/52* | (2006.01) | |
| *A61K 9/00* | (2006.01) | |

(52) U.S. Cl.
CPC ........ *A61K 31/7068* (2013.01); *A61K 9/0053* (2013.01); *A61K 31/52* (2013.01)

(58) Field of Classification Search
CPC ... A61K 31/7068; A61K 31/52; A61K 9/0053
See application file for complete search history.

(56) References Cited

U.S. PATENT DOCUMENTS

| | | | |
|---|---|---|---|
| 5,616,567 A | 4/1997 | Sasaki et al. | |
| 5,654,420 A | 8/1997 | Matsuda et al. | |
| 5,691,319 A | 11/1997 | Kaneko et al. | |
| 6,221,873 B1 | 4/2001 | Havlicek et al. | |
| 6,316,456 B1 | 11/2001 | Meijer et al. | |
| 6,703,395 B2 | 3/2004 | Havlicek et al. | |
| 6,908,906 B2 | 6/2005 | Takita et al. | |
| 7,772,207 B2 | 8/2010 | Green et al. | |
| 8,124,593 B2 | 2/2012 | Gianella-Borradori et al. | |
| 8,163,762 B2 | 4/2012 | Meijer et al. | |
| 8,349,792 B2 | 1/2013 | Green et al. | |
| 8,497,291 B2 | 7/2013 | Westwood et al. | |
| 8,530,445 B2 | 9/2013 | Green et al. | |

(Continued)

FOREIGN PATENT DOCUMENTS

| | | |
|---|---|---|
| WO | 97/20842 A1 | 6/1997 |
| WO | 2005/053699 A1 | 6/2005 |
| WO | 2008/132443 A1 | 11/2008 |

OTHER PUBLICATIONS

Danesi et al., "Pharmacogenetic determinants of anti-cancer drug activity and toxicity" Trends in Pharamcological Sciences (2001) vol. 22 No. 8, pp. 420-426.*
The Merck Manual of Diagnosis and Therapy, seventeenth edition, 1999, Published by Merck Research Laboratories, pp. 397-398, 948-949, 1916, and 1979-1981.*
The Oxford Textbook of Oncology, 1995, published by Oxford University Press, pp. 447-453.*
Hryniuk et al., J. Clin. Oncol., 1984, 2(11), p. 1281-1288.*
Hanahan et al., J. Clin. Invest., 2000, 105(8), p. 1045-1047.*
Holt et al., Nature Genetics, 1996, 12, p. 298-302.*
Meijer et al., Acc. Chem. Res, 2003, 36, p. 417-425.*
Berge S. et al., "Pharmaceutical Salts," Journal of Pharmaceutical Sciences, vol. 66(1), pp. 1-19 (1977).
Burch P. et al. "Phase I Study of Orally Administered CS-682 in Solid Tumors," Proceedings of ASCO, vol. 20, Abstract 364, 1 page (2001)
Donehower R., "A Phase I Study of CS-682, an Oral Antimetabolite, in Patients with Refractory Solid Tumors," Proceedings of ASCO, vol. 19, Abstract 764, 2 pages (2000).

(Continued)

*Primary Examiner* — Jonathan S Lau
(74) *Attorney, Agent, or Firm* — Nelson Mullins Riley & Scarborough LLP; Cynthia L. Kanik; Adam J. Gastonguay

(57) ABSTRACT

A first aspect of the invention relates to a method of treating a proliferative disorder in a subject, said method comprising administering to the subject a therapeutically effective amount of (i) sapacitabine, or a metabolite thereof; and (ii) seliciclib; in accordance with a dosing regimen comprising at least one first treatment cycle and at least one second treatment cycle, wherein said first treatment cycle comprises: (a) administering a therapeutically effective amount of sapacitabine, or a metabolite thereof, for 3 to 5 consecutive days for 2 weeks, starting on day d, where d is the first day of treatment with sapacitabine, or the metabolite thereof, in said first treatment cycle; and (b) optionally administering a therapeutically effective amount of seliciclib for 3 to 5 consecutive days for 2 weeks, starting on day (d−1) relative to the administration of sapacitabine or the metabolite thereof, in said first treatment cycle; followed by a rest period of at least 2 weeks, or until treatment-related toxicities are resolved, whichever is longer; and wherein said second treatment cycle comprises: (a) administering a therapeutically effective amount of sapacitabine, or a metabolite thereof, for 3 to 5 consecutive days for 2 weeks, starting on day d, where d is the first day of treatment with sapacitabine, or the metabolite thereof, in said second treatment cycle; and (b) administering a therapeutically effective amount of seliciclib for 3 to 5 consecutive days for 2 weeks, starting on day (d−1) relative to the administration of sapacitabine or the metabolite thereof, in said second treatment cycle; followed by a rest period of at least 2 weeks, or until treatment-related toxicities are resolved, whichever is longer. Further aspects of the invention relate to a kit of parts, and corresponding uses.

11 Claims, No Drawings

(56) References Cited

U.S. PATENT DOCUMENTS

| | | | |
|---|---|---|---|
| 8,536,188 | B2 | 9/2013 | Chiao |
| 8,809,350 | B2 | 8/2014 | Benigni et al. |
| 8,884,001 | B2 | 11/2014 | Wood et al. |
| 8,975,239 | B2 | 3/2015 | Green et al. |
| 9,173,938 | B2 | 11/2015 | Green et al. |
| 9,675,631 | B2 | 6/2017 | Chiao |
| 2005/0153991 | A1 | 7/2005 | Gianella-Borradori et al. |
| 2005/0164976 | A1 | 7/2005 | Green et al. |
| 2005/0261260 | A1 | 11/2005 | Gianella-Borradori |
| 2005/0267066 | A1 | 12/2005 | Gianella-Borradori |
| 2005/0276866 | A1 | 12/2005 | Gianella-Borradori |
| 2005/0277656 | A1 | 12/2005 | Gianella-Borradori |
| 2006/0148828 | A1 | 7/2006 | Gianella-Borradori et al. |
| 2007/0270442 | A1 | 11/2007 | Green et al. |
| 2007/0287718 | A1 | 12/2007 | Green et al. |
| 2008/0125404 | A1 | 5/2008 | Benigni et al. |
| 2009/0118315 | A1 | 5/2009 | Gianella-Borradori et al. |
| 2009/0274773 | A1 | 11/2009 | Green et al. |
| 2013/0196938 | A1 | 8/2013 | Green et al. |
| 2014/0094428 | A1 | 4/2014 | Chiao |
| 2014/0142058 | A1 | 5/2014 | Chiao |

OTHER PUBLICATIONS

Federico M. et al., "R-Roscovitine (Seliciclib) prevents DNA damage-induced cyclin A1 upregulation and hinders non-homologous end joining (NHEJ) DNA repair," Molecular Cancer, vol. 9, 208, 39 pages (2010).
Frame S. et al., "DNA Repair Defects Enhance Tumor Cell Sensitivity to Sapacitabine," Proceedings of the 103rd Annual Meeting of the American Association for Cancer Research; Mar. 31-Apr. 4, 2012; Chicago, IL, AACR; Cancer Research; vol. 72(8 Suppl), Abstract # 5666, 1 page (2012).
Gray N. et al., "ATP-site Directed Inhibitors of Cyclin-dependent Kinases," Current Medicinal Chemistry, vol. 6, pp. 859-875 (1999).
Hanaoka K. et al., Antitumor Activity and Novel DNA-Self-Strand-Breaking Mechanism of CNDAC (1-(2-C-Cyano-2-Deoxy-β-D-Arabino -pentofuranosyl) cytosine) and its N4-palmitoyl derivative (CS-682), Int J Cancer, vol. 82, pp. 226-236 (1999).
International Preliminary Report on Patentability, PCT/GB2013/051236, dated Nov. 18, 2014, pp. 1-8.
International Search Report and Written Opinion, PCT/GB2013/051236, dated Jan. 7, 2013, pp. 1-11.
Liu X et al., "Homologous Recombination as a Resistance Mechanism to Replication-induced Double-strand Breaks Caused by the Antileukemia Agent CNDAC," Blood, vol. 116 (10), pp. 1737-1746 (2010).
Liu X. et al., "Molecular Basis for G2 Arrest induced by 2'-C-Cyano-2'-Deoxy-1-β-D-Arabino -Pentofuranosylcytosine and Consequences of Checkpoint Abrogation," Cancer Research, vol. 65(15) pp. 6874-6881 (2005).
MacCallum D., et al., "Seliciclib (CYC202, R-Roscovitine) Induces Cell Death in Multiple Myeloma Cells by Inhibition of RNA Polymerase II-Dependent Transcription and Down -Regulation of Mcl-1," Cancer Research, vol. 65(12), pp. 5399-5407 (2005).
Maggiorella, L. et al., "Enhancement of Radiation Response by Roscovitine in Human Breast Carcinoma in Vitro and in Vivo," Cancer Research, vol. 63, pp. 2513-2517 (2003).
Shapiro, G. et al., "Drug Combo Gets Second Wind in Treating BRCA-Deficient Tumors," Cancer Discovery, vol. 3(5) 2 pages, (2013).
Wu, M. et al., "High-Resolution Magnetic Resonance Imaging of the Efficacy of the Cytosine Analogue 1-[2-C-Cyano-2-deoxy-β-d-arabino-pentfuranosyl]-N4-palmitoyl Cytosine (CS-682) in a Liver-Metastasis Athymic Nude Mouse Model," Cancer Research, vol. 23, pp. 2477-2482 (2003).
American Association for Cancer Research, "Drug Combo Gets Second Wind in Treating BRCA-Deficient Tumors," retrieved online at: http://cancerdiscovery.aacrjournals.org/content/3/5/OF4.full, 2 pages (2013)
Serova, M. et al., "Antiproliferative effects of sapacitabine (CYC682), a novel 2'-deoxycytidine-derivative, in human cancer cells," British Journal of Cancer, vol. 97:628-636 (2007).
U.S. Appl. No. 10/581,585, filed Apr. 20, 2007, Simon Richard Green.
U.S. Appl. No. 12/093,427, filed Sep. 8, 2008, Simon Green.
U.S. Appl. No. 12/097,912, filed Sep. 19, 2008, Robert Westwood.
U.S. Appl. No. 12/517,196, filed Nov. 19, 2009, Simon Green.
U.S. Appl. No. 13/709,883, filed Dec. 10, 2012, Simon Green.
U.S. Appl. No. 12/597,293, filed Oct. 23, 2009, Judy Chiao.
U.S. Appl. No. 13/967,901, filed Aug. 15, 2013, Judy Chiao.
U.S. Appl. No. 12/265,553, filed Nov. 5, 2008, Athos Gianella-Borradori.
U.S. Appl. No. 12/991,582, filed Apr. 29, 2011, Gavin Wood.
U.S. Appl. No. 12/997,197, filed Apr. 5, 2011, Simon Richard Green.
U.S. Appl. No. 13/960,489, filed Aug. 6, 2013, Simon Richard Green.
U.S. Appl. No. 14/111,430, filed Dec. 17, 2013, Judy H. Chiao.
U.S. Appl. No. 12/573,358, filed Oct. 5, 2009, Simon Green.
Cyclacel Phamaceuticals, Press Release, "Cyclacel Reports Updated Data From Its DNA Damage Response Program on Seliciclib and Sapacitabine Combination in Patients With Solid Tumors at ASCO," Jun. 6, 2016, 2 pages.
Letourneau, C. et al., "Phase 1 Evaluation of Seliciclib (R-roscovitine), a novel oral cyclin-dependent kinase inhibitor, in patients with advanced malignancies," European Journal of Cancer, vol. 46:3243-3250 (2010).
Tolcher A. et al., "Phase 1 study of sapacitabine, an oral nucleoside analogue in patients with refractory solid tumors or lymphomas," European Journal of Cancer, vol. 4 (12): Abstract 463, 142 (2006).

* cited by examiner

DOSAGE REGIMEN FOR SAPACITABINE AND SELICICLIB

RELATED APPLICATIONS

This application is a 35 U.S.C. 371 national stage filing of International Application No. PCT/GB2013/051236, filed May 14, 2013, which claims foreign priority to United Kingdom Application No. 1304599.2, filed Mar. 14, 2013, which claims prioriy to United Kingdom Application No. 1208536.1, filed May 15, 2012. The contents of each of the aforementioned applications are hereby incorporated by reference.

FIELD OF THE INVENTION

The present invention relates to a dosing regimen suitable for the treatment of cancer and other proliferative disorders.

BACKGROUND TO THE INVENTION

Initiation, progression, and completion of the mammalian cell cycle are regulated by various cyclin-dependent kinase (CDK) complexes, which are critical for cell growth. These complexes comprise at least a catalytic (the CDK itself) and a regulatory (cyclin) subunit. Some of the more important complexes for cell cycle regulation include cyclin A (CDK1—also known as cdc2, and CDK2), cyclin B1-B3 (CDK1), cyclin C (CDK8), cyclin D1-D3 (CDK2, CDK4, CDK5, CDK6), cyclin E (CDK2), cyclins K and T (CDK9) and cyclin H (CDK7). Each of these complexes is involved in a particular phase of the cell cycle or in the regulation of transcription.

The activity of CDKs is regulated post-translationally, by transitory associations with other proteins, and by alterations of their intracellular localisation. Tumour development is closely associated with genetic alteration and deregulation of CDKs and their regulators, suggesting that inhibitors of CDKs may be useful anti-cancer therapeutics. Indeed, early results suggest that transformed and normal cells differ in their requirement for e.g. cyclin A/CDK2 and that it may be possible to develop novel antineoplastic agents devoid of the general host toxicity observed with conventional cytotoxic and cytostatic drugs.

The function of CDKs is to phosphorylate and thus activate or deactivate certain proteins, including e.g. retinoblastoma proteins, lamins, histone H1, and components of the mitotic spindle. The catalytic step mediated by CDKs involves a phospho-transfer reaction from ATP to the macromolecular enzyme substrate. Several groups of compounds (reviewed in e.g. N. Gray, L. Détivaud, C. Doerig, L. Meijer, *Curr. Med. Chem.* 1999, 6, 859) have been found to possess anti-proliferative properties by virtue of CDK-specific ATP antagonism.

Seliciclib is the compound 6-benzylamino-2-[(R)-1-ethyl-2-hydroxyethylamino]-9-isopropylpurine. Seliciclib has been demonstrated to be a potent inhibitor of cyclin dependent kinase enzymes, particularly CDK2. This compound is currently in development as an anti-cancer agent. CDK inhibitors are understood to block passage of cells from the G2/M phase of the cell cycle.

It is well established in the art that active pharmaceutical agents can often be given in combination in order to optimise the treatment regime. For example, WO 2005/053699 (Cyclacel Limited) discloses a pharmaceutical combination comprising sapacitabine and seliciclib, and methods of treatment using the same. More specifically, WO 2005/053699 discloses methods of treating proliferative disorders selected from lung, prostate, bladder, head and neck and colon cancer, sarcoma and lymphoma by sequentially administering sapacitabine and seliciclib.

The present invention seeks to provide a new dosing regimen for known pharmaceutical agents that is particularly suitable for the treatment of proliferative disorders, especially cancer. More specifically, the invention centres on the surprising and unexpected effects associated with using certain pharmaceutical agents in combination in a particular dosing regimen.

STATEMENT OF INVENTION

In a first aspect, the invention provides a method of treating a proliferative disorder in a subject, said method comprising administering to the subject a therapeutically effective amount of (i) sapacitabine, or a metabolite thereof; and (ii) seliciclib; in accordance with a dosing regimen comprising at least one first treatment cycle and at least one second treatment cycle, wherein said first treatment cycle comprises:
(a) administering a therapeutically effective amount of sapacitabine, or a metabolite thereof, for 3 to 5 consecutive days for 2 weeks, starting on day d, where d is the first day of treatment with sapacitabine, or the metabolite thereof, in said first treatment cycle; and
(b) optionally administering a therapeutically effective amount of seliciclib for 3 to 5 consecutive days for 2 weeks, starting on day (d−1) relative to the administration of sapacitabine or the metabolite thereof, in said first treatment cycle;

followed by a rest period of at least 2 weeks, or until treatment-related toxicities are resolved, whichever is longer; and wherein said second treatment cycle comprises:
(a) administering a therapeutically effective amount of sapacitabine, or a metabolite thereof, for 3 to 5 consecutive days for 2 weeks, starting on day d, where d is the first day of treatment with sapacitabine, or the metabolite thereof, in said second treatment cycle; and
(b) administering a therapeutically effective amount of seliciclib for 3 to 5 consecutive days for 2 weeks, starting on day (d−1) relative to the administration of sapacitabine or the metabolite thereof, in said second treatment cycle;

followed by a rest period of at least 2 weeks, or until treatment-related toxicities are resolved, whichever is longer.

A second aspect of the invention relates to the use of (i) sapacitabine, or a metabolite thereof; and (ii) seliciclib; in the preparation of a medicament for treating a proliferative disorder, wherein the sapacitabine, or metabolite thereof, and the seliciclib are administered in accordance with a dosing regimen comprising at least one first treatment cycle and at least one second treatment cycle, wherein said first treatment cycle comprises:
(a) administering a therapeutically effective amount of sapacitabine, or a metabolite thereof, for 3 to 5 consecutive days for 2 weeks, starting on day d, where d is the first day of treatment with sapacitabine, or the metabolite thereof, in said first treatment cycle; and
(b) optionally administering a therapeutically effective amount of seliciclib for 3 to 5 consecutive days for 2 weeks, starting on day (d−1) relative to the administration of sapacitabine or the metabolite thereof, in said first treatment cycle;

followed by a rest period of at least 2 weeks, or until treatment-related toxicities are resolved, whichever is longer; and wherein said second treatment cycle comprises:
(a) administering a therapeutically effective amount of sapacitabine, or a metabolite thereof, for 3 to 5 consecutive days for 2 weeks, starting on day d, where d is the first day of treatment with sapacitabine, or the metabolite thereof, in said second treatment cycle; and
(b) administering a therapeutically effective amount of seliciclib for 3 to 5 consecutive days for 2 weeks, starting on day (d−1) relative to the administration of sapacitabine or the metabolite thereof, in said second treatment cycle;

followed by a rest period of at least 2 weeks, or until treatment-related toxicities are resolved, whichever is longer.

A third aspect of the invention relates to (i) sapacitabine, or a metabolite thereof; and (ii) seliciclib; for use in treating a proliferative disorder, wherein the sapacitabine, or a metabolite thereof, and the seliciclib are administered in accordance with a dosing regimen comprising at least one first treatment cycle and at least one second treatment cycle, wherein said first treatment cycle comprises:
(a) administering a therapeutically effective amount of sapacitabine, or a metabolite thereof, for 3 to 5 consecutive days for 2 weeks, starting on day d, where d is the first day of treatment with sapacitabine, or the metabolite thereof, in said first treatment cycle; and
(b) optionally administering a therapeutically effective amount of seliciclib for 3 to 5 consecutive days for 2 weeks, starting on day (d−1) relative to the administration of sapacitabine or the metabolite thereof, in said first treatment cycle; and followed by a rest period of at least 2 weeks, or until treatment-related toxicities are resolved, whichever is longer; and wherein said second treatment cycle comprises:
(a) administering a therapeutically effective amount of sapacitabine, or a metabolite thereof, for 3 to 5 consecutive days for 2 weeks, starting on day d, where d is the first day of treatment with sapacitabine, or the metabolite thereof, in said second treatment cycle; and
(b) administering a therapeutically effective amount of seliciclib for 3 to 5 consecutive days for 2 weeks, starting on day (d−1) relative to the administration of sapacitabine or the metabolite thereof, in said second treatment cycle;

followed by a rest period of at least 2 weeks, or until treatment-related toxicities are resolved, whichever is longer.

A fourth aspect of the invention relates to a kit of parts comprising:
(i) sapacitabine, or a metabolite thereof;
(ii) seliciclib and
(iii) instructions for administering sapacitabine, or a metabolite thereof, and seliciclib in accordance with a dosing regimen comprising at least one first treatment cycle and at least one second treatment cycle,
wherein said first treatment cycle comprises:
(a) administering a therapeutically effective amount of sapacitabine, or a metabolite thereof, for 3 to 5 consecutive days for 2 weeks, starting on day d, where d is the first day of treatment with sapacitabine, or the metabolite thereof, in said first treatment cycle; and
(b) optionally administering a therapeutically effective amount of seliciclib for 3 to 5 consecutive days for 2 weeks, starting on day (d−1) relative to the administration of sapacitabine or the metabolite thereof, in said first treatment cycle;

followed by a rest period of 2 weeks, or until treatment-related toxicities are resolved, whichever is longer; and
wherein said second treatment cycle comprises:
(a) administering a therapeutically effective amount of sapacitabine, or a metabolite thereof, for 3 to 5 consecutive days for 2 weeks, starting on day d, where d is the first day of treatment with sapacitabine, or the metabolite thereof, in said second treatment cycle; and
(b) administering a therapeutically effective amount of seliciclib for 3 to 5 consecutive days for 2 weeks, starting on day (d−1) relative to the administration of sapacitabine or the metabolite thereof, in said second treatment cycle;

followed by a rest period of 2 weeks, or until treatment-related toxicities are resolved, whichever is longer.

A fifth aspect of the invention relates to a kit of parts as described above for treating a proliferative disorder in a subject.

DETAILED DESCRIPTION

The preferred embodiments as set out below are applicable to all the above-mentioned aspects of the invention.

As mentioned above, the present invention provides a new dosing regimen for sapactiabine and seliciclib that is particularly effective in the treatment of proliferative disorders. More specifically, the dosing regimen involves a first and second treatment cycles, wherein at least the second treatment cycle involves the overlapping administration of seliciclib and sapacitabine, wherein the seliciclib is administered a short time (e.g. about 8-24 hours) before the sapacitabine. This regimen is thought to allow for the transcriptional effects of seliciclib on cancer cells to be in effect both before and after the sapacitabine dose administration, maximising the inhibitory effect on DNA repair pathways.

It is well known that the effect of drug combinations is inherently unpredictable and there is often a propensity for one drug to partially or completely inhibit the effects of the other. The present invention is based on the surprising observation that administering sapacitabine and seliciclib in combination with a particular dosing regimen does not lead to any adverse interaction between the two agents. The unexpected absence of any such antagonistic interaction is critical for clinical applications.

In fact studies by the Applicant have shown that administering sapacitabine and seliciclib in accordance with the above-described dosing regimen gives rise to an enhanced effect as compared to either drug administered alone. The surprising nature of this observation is in contrast to that expected on the basis of the prior art. In particular, the administration of sapacitabine and seliciclib in accordance with the presently claimed dosing regimen maximizes the efficacy of both drugs and does not result in any exacerbation of the toxicities associated with each drug.

1-(2-C-cyano-2-dioxy-β-D-arabino-pentofuranosyl)-$N^4$-palmitoyl cytosine (I), also known as 2'-cyano-2-deoxy-$N^4$-palmitoyl-1-β-D-arabinofuranosylcytosine (Hanaoka, K., et al, *Int. J. Cancer*, 1999:82:226-236; Donehower R, et al, *Proc Am Soc Clin Oncol*, 2000: abstract 764; Burch, P A, et al, *Proc Am Soc Clin Oncol*, 2001: abstract 364) or "sapacitabine", is an orally administered novel 2'-deoxycytidine antimetabolite prodrug of the nucleoside CNDAC, 1-(2-C-Cyano-2-deoxy-β-D-arabino-pentafuranosyl)-cytosine.

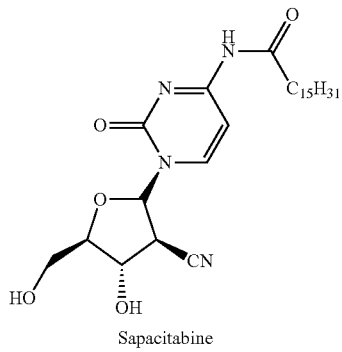

Sapacitabine

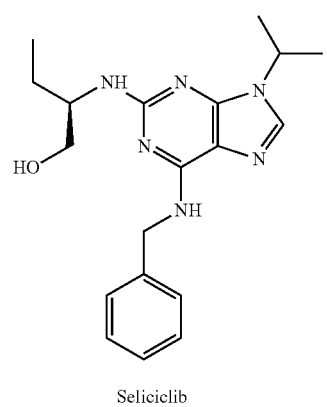 [SMILES: CC[C@H](CO)Nc1nc(NCc2ccccc2)c2ncn(C(C)C)c2n1]

Seliciclib

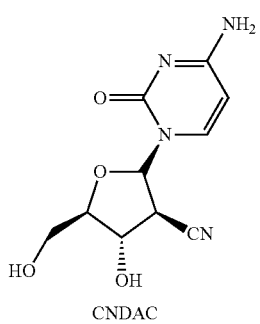

CNDAC

Sapacitabine has a unique mode of action over other nucleoside metabolites such as gemcitabine in that it has a spontaneous DNA strand breaking action, resulting in potent anti-tumour activity in a variety of cell lines, xenograft and metastatic cancer model. The active metabolite CNDAC generates single strand DNA breaks. It has been demonstrated that DNA single-strand breaks generated following CNDAC incorporation can be transformed into DNA double-strand breaks during subsequent rounds of replication (Liu et al, Cancer Res 2005; 65 (15) August 1, 6874-6881; Liu et al, Blood, 9 Sep. 2010; Col 116; No. 10; 1737-1746). Repair of CNDAC-induced DNA breaks is dependent on components of these DSB repair pathways and, in particular, defects in homologous recombination (HR) repair have been shown to sensitize cell lines to CNDAC (Liu et al, 2010 ibid).

Sapacitabine has been the focus of a number of studies in view of its oral bioavailability and its improved activity over gemcitabine (the leading marketed nucleoside analogue) and 5-FU (a widely-used antimetabolite drug) based on preclinical data in solid tumours. Recently, investigators reported that sapacitabine exhibited strong anticancer activity in a model of colon cancer. In the same model, sapacitabine was found to be superior to either gemcitabine or 5-FU in terms of increasing survival and also preventing the spread of colon cancer metastases to the liver (Wu M, et al, *Cancer Research,* 2003:63:2477-2482). To date, phase I data from patients with a variety of cancers suggest that sapacitabine is well tolerated in humans, with myelosuppression as the dose limiting toxicity.

Seliciclib (or "CYC202") is a 2,6,9-substituted purine analog having the structure shown below:

Seliciclib and related purines were first described in WO97/20842. Seliciclib is a selective and potent inhibitor of CDK2/cyclin E, CDK7/cyclin H and CDK9/cyclin T. The activity against CDK2 results in effects on the cell cycle, while the activity against CDK7/cyclin H and CDK9/cyclin K/T1 results in an effect on transcriptional regulation. Treatment of cell lines has wide-ranging effects including: accumulation of cells in G1 and G2 phases, inhibition of rRNA processing, inhibition of RNA polymerase II-dependent transcription, disruption of nucleoli, and induction of apoptosis from all stages of the cell cycle. In myeloma cells, seliciclib causes myeloma cell death by disrupting the balance between cell survival and apoptosis through the inhibition of transcription and down-regulation of myeloid leukemia cell sequence 1 protein (Mcl-1). (MacCallum et al, Cancer Res 2005, June 15, 65(12) 5399-5407).

CDK inhibition has also been shown to potentially affect the two major DSB repair pathways—homologous recombination (HR) and non-homologous end-joining (NHEJ) and it has also been demonstrated that CDK inhibition can potentiate the effect of DNA damaging agents such as doxorubicin, sapacitabine and gamma irradiation (Maggiorella et al, Cancer Research, 63, 2513-2517, May 15, 2003; Federico et al, Molecular Cancer 2010l 9; 208). Twenty-four hour treatment of A549 cells with seliciclib caused significant downregulation of key genes involved in HR (BRCA1 and RAD50) and NHEJ (Ku80, DNA-PK and NHEJ1) leading to the inhibition of these DNA repair pathways (Federico et al, 2010 ibid).

In vitro studies in cell lines have shown that combination treatments of sapacitabine and seliciclib are most synergistic in inducing cell death when used sequentially rather than concomitantly. However, these studies cannot indicate what adverse effects on the toxicities of the compounds will occur when they are used together (Frame et al, Proc Am Assoc Cancer Res 2012; 53, Abs 5666). Combination treatments of sapacitabine and seliciclib could be synergistic in cell lines due to more than one mechanism including: (i) decreased apoptotic threshold through altered expression of apoptotic regulators; (ii) cell cycle effects leading to cell death; and (iii) suppression of DNA repair processes through transcriptional downregulation of repair proteins and additional induction of DNA damage. Each of these mechanisms could require a different clinical dosing schedule of the two drugs to be optimally active.

Surprisingly, the Applicant has found that combining seliciclib and sapacitabine in the order of seliciclib treatment given 8-12 hours prior to sapacitabine treatment is effective and does not result in unexpected or exacerbated toxicities due to the combination of the two drugs.

Dosing Regimen

As mentioned above, the present invention relates to a method of treating a proliferative disorder in a subject, said method comprising administering to the subject a therapeutically effective amount of (i) sapacitabine, or a metabolite thereof; and (ii) seliciclib; in accordance with a dosing regimen (hereinafter referred to as "Schedule 1") comprising at least one first treatment cycle and at least one second treatment cycle, wherein said first treatment cycle comprises:
(a) administering a therapeutically effective amount of sapacitabine, or a metabolite thereof, for 3 to 5 consecutive days for 2 weeks, starting on day d, where d is the first day of treatment with sapacitabine, or the metabolite thereof, in said first treatment cycle; and
(b) optionally administering a therapeutically effective amount of seliciclib for 3 to 5 consecutive days for 2 weeks, starting on day (d−1) relative to the administration of sapacitabine or the metabolite thereof, in said first treatment cycle;
followed by a rest period of at least 2 weeks, or until treatment-related toxicities are resolved, whichever is longer; and wherein said second treatment cycle comprises:
(a) administering a therapeutically effective amount of sapacitabine, or a metabolite thereof, for 3 to 5 consecutive days for 2 weeks, starting on day d, where d is the first day of treatment with sapacitabine, or the metabolite thereof, in said second treatment cycle; and
(b) administering a therapeutically effective amount of seliciclib for 3 to 5 consecutive days for 2 weeks, starting on day (d−1) relative to the administration of sapacitabine or the metabolite thereof, in said second treatment cycle;
followed by a rest period of at least 2 weeks, or until treatment-related toxicities are resolved, whichever is longer.

In one preferred embodiment, the first treatment cycle comprises:
(a) administering a therapeutically effective amount of sapacitabine, or a metabolite thereof, on days 1 to 5, and days 8 to 12, starting on day d, where d is the first day of treatment with sapacitabine, or the metabolite thereof, in said first treatment cycle; and
(b) optionally administering a therapeutically effective amount of seliciclib on day (d−1) to day 4, and days 7 to 11, starting on day (d−1) relative to the administration of sapacitabine or the metabolite thereof, in said first treatment cycle; and the second treatment cycle comprises:
(a) administering a therapeutically effective amount of sapacitabine, or a metabolite thereof, on days 1 to 5, and days 8 to 12, starting on day d, where d is the first day of treatment with sapacitabine, or the metabolite thereof, in said second treatment cycle; and
(b) administering a therapeutically effective amount of seliciclib on day (d−1) to day 4, and days 7 to 11, starting on day (d−1) relative to the administration of sapacitabine or the metabolite thereof, in said second treatment cycle;
followed by a rest period of at least 2 weeks, or until treatment-related toxicities are resolved, whichever is longer.

In another preferred embodiment, the first treatment cycle comprises administering a therapeutically effective amount of sapacitabine only, or a metabolite thereof, and the second treatment cycle comprises administering sapacitabine in combination with seliciclib.

In a more preferred embodiment, the first treatment cycle comprises administering a therapeutically effective amount of sapacitabine, or a metabolite thereof, for 3 to 5 consecutive days for 2 weeks, followed by a rest period of at least 2 weeks, or until treatment-related toxicities are resolved, whichever is longer.

In one preferred embodiment, the first treatment cycle comprises administering a therapeutically effective amount of sapacitabine, or a metabolite thereof, for 5 consecutive days for 2 weeks, followed by a rest period of at least 2 weeks, or until treatment-related toxicities are resolved, whichever is longer.

In one preferred embodiment, the first treatment cycle comprises administering a therapeutically effective amount of sapacitabine, or a metabolite thereof, on days 1 to 5, no drug on days 6 and 7, and administering a therapeutically effective amount of sapacitabine, or a metabolite thereof, on days 8 to 12, followed by a rest period of at least 2 weeks, or until treatment-related toxicities are resolved, whichever is longer.

In one preferred embodiment, the second treatment cycle comprises:
(a) administering a therapeutically effective amount of sapacitabine, or a metabolite thereof, for 5 consecutive days for 2 weeks, starting on day d, where d is the first day of treatment with sapacitabine, or the metabolite thereof, in said second treatment cycle; and
(b) administering a therapeutically effective amount of seliciclib for 5 consecutive days for 2 weeks, starting on day (d−1) relative to the administration of sapacitabine or the metabolite thereof, in said second treatment cycle;
followed by a rest period of at least 2 weeks, or until treatment-related toxicities are resolved, whichever is longer.

In one preferred embodiment, the second treatment cycle comprises:
(a) administering a therapeutically effective amount of sapacitabine, or a metabolite thereof, on days 1 to 5 of second treatment cycle; and
(b) administering a therapeutically effective amount of seliciclib on days −1 to 4 second treatment cycle relative to the administration of sapacitabine or the metabolite thereof, in said second treatment cycle;
followed by a rest period of at least 2 weeks, or until treatment-related toxicities are resolved, whichever is longer.

In one preferred embodiment, the first treatment cycle is 28 days in length.

In one preferred embodiment, the second treatment cycle is 28 days in length.

In one preferred embodiment, the dosing regimen comprises a first treatment cycle, followed by two or more of said second treatment cycles, more preferably, three or more, four or more, or five or more of said second treatment cycles.

In one preferred embodiment, the dosing regimen comprises a first treatment cycle, followed by two to four of said second treatment cycles.

The treatment cycles are repeated sequentially and include rest periods between the periods of drug administration. For example, there is a rest period between the last day of drug administration of the first treatment cycle and the first day of drug administration of the second treatment cycle. Preferably, the rest period is sufficient so as to resolve any treatment-related toxicities. As used herein, treatment-related toxicities are mostly myelosuppression and its associated complications.

For example, in one preferred embodiment, the rest period is 16 days (i.e. 16 drug-free days) from the last day of sapacitabine administration of any one treatment cycle to the first day of sapacitabine administration of the subsequent treatment cycle. Alternatively, the rest period is 16 days from the last day of seliciclib administration of any one treatment cycle to the first day of seliciclib administration of the subsequent treatment cycle. Alternatively, the rest period is 15 days from the last day of sapacitabine administration of any one treatment cycle to the first day of seliciclib administration of the subsequent treatment cycle.

In one preferred embodiment, the seliciclib is administered orally.

In one preferred embodiment, the seliciclib is administered in a dose of from about 200 mg to about 800 mg per day, more preferably from about 400 to about 600 mg per day.

In one preferred embodiment, the seliciclib is administered once daily (q.d.).

In one preferred embodiment, the seliciclib is administered once daily (q.d.) in a dose of about 200 mg.

In one preferred embodiment, the sapacitabine, or metabolite thereof, is administered orally.

In one preferred embodiment, the sapacitabine or metabolite thereof is administered in a dose of about 50 mg to about 300 mg per day, more preferably from about 100 to about 250 mg per day.

In one preferred embodiment, the sapacitabine, or metabolite thereof, is administered once daily (q.d.).

In one preferred embodiment, the sapacitabine or metabolite thereof is administered once daily (q.d.) in a dose of about 150 mg to 200 mg.

In one preferred embodiment, the seliciclib is administered to the subject at least about 4 hours prior to the sapacitabine, or metabolite thereof, more preferably, at least about 6 hours, even more preferably, at least about 8 hours prior to the sapacitabine, or metabolite thereof.

In one preferred embodiment, the seliciclib is administered to the subject about 8 to about 12 hours prior to the sapacitabine, or metabolite thereof.

In one preferred embodiment, the seliciclib is administered to the subject in the evening and the sapacitabine, or metabolite thereof, is administered the following morning, preferably where the administration of seliciclib is at least 8 hours prior to the administration of the sapacitabine, or metabolite thereof.

In one highly preferred embodiment, the first treatment cycle comprises administering sapacitabine for 5 consecutive days a week for 2 weeks at a starting dose of 150 mg once daily (q.d.) on days 1-5 and 8-11 given in the morning, and the second and each subsequent treatment cycle comprises administering sapacitabine for 5 consecutive days a week for 2 weeks at a starting dose of 150 mg once daily (q.d.) on days 1-5 and 8-11 given in the morning and adding seliciclib on days −1 to 4 and 7-10 of the second treatment cycle at a starting dose of 400 mg, once daily (q.d.) given in the evening, wherein each treatment cycle is 28 days in length.

In another highly preferred embodiment, the dosing regimen comprises a first treatment cycle comprising administering sapacitabine for 5 consecutive days a week for 2 weeks at a starting dose of 150 mg once daily (q.d.) on days 1-5 and 8-11 given in the morning, and administering seliciclib on days −1 to 4 and 7-10 at a starting dose of 400 mg, once daily (q.d.) given in the evening, wherein the treatment cycle is 28 days in length, and wherein the dosing regimen comprises repeating said first treatment cycle two or more times.

In one preferred embodiment, the seliciclib and sapacitabine are each administered in a therapeutically effective amount with respect to the individual components; in other words, the seliciclib and sapacitabine are administered in amounts that would be therapeutically effective even if the components were administered other than in combination.

In one preferred embodiment, the seliciclib and sapacitabine are each administered in a sub-therapeutic amount with respect to the individual components; in other words, the seliciclib and sapacitabine are administered in amounts that would be therapeutically ineffective if the components were administered other than in combination.

Preferably, the sapacitabine and seliciclib interact in a synergistic manner. As used herein, the term "synergistic" means that sapacitabine and the seliciclib produce a greater effect when used in combination than would be expected from adding the individual effects of the two components. Advantageously, a synergistic interaction may allow for lower doses of each component to be administered to a patient, thereby decreasing the toxicity of chemotherapy, whilst producing and/or maintaining the same therapeutic effect. Thus, in a particularly preferred embodiment, each component can be administered in a sub-therapeutic amount.

In an alternative embodiment (hereinafter referred to as "Schedule 2"), the invention relates to a method of treating a proliferative disorder in a subject, said method comprising administering to the subject a therapeutically effective amount of (i) sapacitabine, or a metabolite thereof; and (ii) seliciclib; in accordance with a dosing regimen comprising at least one treatment cycle, wherein said treatment cycle comprises:

(a) administering a therapeutically effective amount of sapacitabine, or a metabolite thereof, for 5 to 9 consecutive days; and (b) administering a therapeutically effective amount of seliciclib for 2 to 5 consecutive days;

followed by a rest period of at least 10 days, or until treatment-related toxicities are resolved, whichever is longer.

Preferably, the seliciclib administered in step (b) is administered after the sapacitabine, or metabolite thereof, in step (a) without a rest period. Preferably, the seliciclib administration starts the day after the sapacitabine administration has been completed, i.e. there are no drug-free days in between.

For Schedule 2, preferably the treatment cycle is 21 days in length.

In one particularly preferred embodiment, the treatment cycle of Schedule 2 comprises:

(a) administering a therapeutically effective amount of sapacitabine, or a metabolite thereof, for 7 consecutive days; followed by (b) administering a therapeutically effective amount of seliciclib for 3 consecutive days;

followed by a rest period of at least 10 days, or until treatment-related toxicities are resolved, whichever is longer.

In one particularly preferred embodiment, the treatment cycle of Schedule 2 comprises:

(a) administering a therapeutically effective amount of sapacitabine, or a metabolite thereof, for 7 consecutive days; followed by (b) administering a therapeutically effective amount of seliciclib for 3 consecutive days;
followed by a rest period of 11 days.

For Schedule 2, preferably the sapacitabine is administered twice daily (bid.).

For Schedule 2, preferably the seliciclib is administered twice daily (bid.).

For Schedule 2, preferably, the treatment cycle is repeated two or more times, more preferably, three or more, four or more, or five or more times.

Proliferative Disorders

The term "proliferative disorder" is used herein in a broad sense to include any disorder that requires control of the cell cycle, for example cardiovascular disorders such as restenosis and cardiomyopathy, auto-immune disorders such as glomerulonephritis and rheumatoid arthritis, dermatological disorders such as psoriasis, anti-inflammatory, anti-fungal, antiparasitic disorders such as malaria, emphysema and alopecia. In these disorders, the compounds of the present invention may induce apoptosis or maintain stasis within the desired cells as required. Preferably, the proliferative disorder is a cancer or leukaemia, most preferably cancer of the lung, prostate, bladder, head and neck, colon, sarcoma or lymphoma.

In one preferred embodiment, the proliferative disorder is a solid tumor, more preferably selected from breast cancer, ovarian cancer, pancreatic cancer, nasopharyngeal cancer, uterine cancer, colon cancer, lung cancer and leiomyosarcoma.

In one preferred embodiment, the cancer is has a germline mutation. As used herein the term "germline mutation" refers to any detectable and heritable variation in the lineage of germ cells. Mutations in these cells are transmitted to offspring, whereas those in somatic cells are not. A germline mutation gives rise to a constitutional mutation in the offspring, that is, a mutation that is present in virtually every cell. High-risk mutations, for example those which disable an important error-free DNA repair process (homology directed repair), significantly increase a subject's risk of developing certain types of cancers.

In one preferred embodiment, the germline mutation is a deleterious mutation and the change is proven to cause significant risks. Often, these are frameshift mutations that prevent the cell from producing more than the first part of the necessary protein. Deleterious mutations have high, but not complete, genetic penetrance, which means that subjects with the mutation have a high risk of developing disease as a result, but that some subjects will not develop cancer despite carrying a harmful mutation.

In one preferred embodiment, the cancer has a BRCA1 and/or a BRCA2 gene mutation.

A BRCA mutation is a mutation in either of the genes BRCA1 and BRCA2. Both BRCA genes are tumor suppressor genes that produce proteins that are used by the cell in an enzymatic pathway that makes very precise, perfectly matched repairs to DNA molecules that have double-stranded breaks. The pathway requires proteins produced by several other genes, including CHEK2, FANCD2 and ATM. Harmful mutations in any of these genes disable the gene or the protein that it produces and give rise to a hereditary breast-ovarian cancer syndrome in affected families. High-risk mutations significantly increase a subject's risk of developing breast cancer, ovarian cancer and certain other cancers. The cancer risk associated with any given mutation varies significantly and depends on the exact type and location of the mutation and possibly other individual factors.

Women with harmful mutations in either BRCA1 or BRCA2 have risk of breast cancer that is about five times the normal risk, and a risk of ovarian cancer that is about ten to thirty times normal. BRCA1 mutations typically confer a higher risk of breast and ovarian cancer in women than BRCA2 mutations. BRCA mutations can also increase the risk of other cancers, such as colon cancer, pancreatic cancer, and prostate cancer. The cancer risk caused by BRCA1 and BRCA2 mutations is inherited in a dominant fashion. A mutated BRCA gene can be inherited from either parent. There are many variations in BRCA genes, and not all changes confer the same risks.

In a particularly preferred embodiment, the invention relates to the use of the dosing regimen described hereinbefore in the treatment of a CDK dependent or sensitive proliferative disorder. CDK dependent disorders are associated with an above normal level of activity of one or more CDK enzymes. Such disorders are preferably associated with an abnormal level of activity of CDK2 and/or CDK4. A CDK sensitive disorder is a disorder in which an aberration in the CDK level is not the primary cause, but is downstream of the primary metabolic aberration. In such scenarios, CDK2 and/or CDK4 can be said to be part of the sensitive metabolic pathway and CDK inhibitors may therefore be active in treating such disorders. Such disorders are preferably cancer or leukaemic disorders.

Surprisingly, the administration of seliciclib in accordance with the presently claimed dosing regimen is able to potentiate the effect of sapacitabine in cancers having a BRCA1 and/or a BRCA2 gene mutation. Cells deficient in components of the HRR pathway, such as BRCA1 and BRCA2 are substantially sensitized to CNDAC (the active metabolite of sapacitabine), thus sapacitabine may be particularly effective in patients with BRCA1/2- or HRR-deficient tumours, such as subsets of triple negative breast, ovarian, non-small cell lung cancer and colon cancer. Moreover, seliciclib has been shown to reduce the expression of BRCA1 and BRCA2, and has been shown to inhibit DSB repair, and which may contribute to the synergistic activity observed with CNDAC and seliciclib.

As used herein the phrase "preparation of a medicament" includes the use of the components of the invention directly as the medicament in addition to their use in any stage of the preparation of such a medicament.

Metabolite

As used herein, the term "metabolite" encompasses chemically modified entities that are produced by metabolism of sapacitabine.

In one particularly preferred embodiment of the invention, the metabolite of sapacitabine is 2'-C'-cyano-2'-dioxy-1-β-D-arabino-pentofuranosyl cytosine (CNDAC).

In another particularly preferred embodiment of the invention, sapacitabine is metabolized intracellularly to the active metabolite CNDAC-triphosphate (CNDACTP), a process involving both the cleavage of the palmitoyl moiety and activation to CNDACTP by the action of nucleoside kinases.

Salts/Esters

The agents of the present invention can be present as salts or esters, in particular pharmaceutically acceptable salts or esters.

Pharmaceutically acceptable salts of the agents of the invention include suitable acid addition or base salts thereof. A review of suitable pharmaceutical salts may be found in Berge et at, J Pharm Sci, 66, 1-19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Enantiomers/Tautomers

The invention also includes where appropriate all enantiomers and tautomers of the agents. The man skilled in the art will recognise compounds that possess an optical properties (one or more chiral carbon atoms) or tautomeric characteristics. The corresponding enantiomers and/or tautomers may be isolated/prepared by methods known in the art.

Stereo and Geometric Isomers

Some of the agents of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those inhibitor agents, and mixtures thereof. The terms used in the claims encompass these forms, provided said forms retain the appropriate functional activity (though not necessarily to the same degree).

The present invention also includes all suitable isotopic variations of the agent or pharmaceutically acceptable salts thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of the agent of the present invention and pharmaceutically acceptable salts thereof of this invention can generally be prepared by conventional procedures using appropriate isotopic variations of suitable reagents.

Solvates

The present invention also includes solvate forms of the agents of the present invention. The terms used in the claims encompass these forms.

Polymorphs

The invention furthermore relates to agents of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Prodrugs

The invention further includes agents of the present invention in prodrug form. Such prodrugs are generally compounds wherein one or more appropriate groups have been modified such that the modification may be reversed upon administration to a human or mammalian subject. Such reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Administration

The pharmaceutical compositions of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration.

For oral administration, particular use is made of compressed tablets, pills, tablets, gellules, drops, and capsules. Preferably, these compositions contain from 1 to 2000 mg and more preferably from 50-1000 mg, of active ingredient per dose.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Injectable forms may contain between 10-1000 mg, preferably between 10-500 mg, of active ingredient per dose.

Compositions may be formulated in unit dosage form, i.e., in the form of discrete portions containing a unit dose, or a multiple or sub-unit of a unit dose.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention. Dosages and frequency of application are typically adapted to the general medical condition of the patient and to the severity of the adverse effects caused, in particular to those caused to the hematopoietic, hepatic and to the renal system.

Depending upon the need, the agent may be administered at a dose of from about 0.1 to about 30 mg/kg body weight, more preferably, from about 2 to about 20 mg/kg body weight, even more preferably from 2 to 15 mg/kg body weight.

By way of guidance, sapacitabine is typically administered at dosages between 50 mg and 300 mg per dose orally. Sapacitabine is typically administered from about 50 mg to 300 mg per dose, more preferably from about 150 mg to 250 mg per dose. Sapacitabine can be administered as a single dose or administered twice a day. Preferably, the sapacitabine is administered once daily in Schedule 1, or twice daily in Schedule 2.

Seliciclib is typically administered from about 200 mg to 1200 mg per dose, more preferably from about 200 mg to 800 mg per dose, even more preferably from about 400 mg to 600 mg per dose. Preferably, seliciclib is administered orally or intravenously. When administered orally, seliciclib is preferably administered in tablets or capsules. Seliciclib can be administered as a single dose or administered twice a day. Preferably, the seliciclib is administered once daily in Schedule 1, or twice daily in Schedule 2.

The present invention is further described by way of example.

EXAMPLES

Methods and Materials

Sapacitabine and seliciclib were manufactured by Cyclacel Limited in accordance with known methodology.
Phase I Study of Sequential Sapacitabine and Seliciclib in Patients with Advanced Solid Tumors A Phase 1 study was undertaken to evaluate sequential sapacitabine and seliciclib.
Methods
Schedule 1:

Cycle 1: Sapacitabine given for 5 days per week for 2 weeks at a starting dose of 150 mg once daily (q.d.) on days 1-5 and 8-11 given in the morning. In cycle 2 and thereafter, adding seliciclib on days −1 to 4 and 7-10 of cycle 2 at a starting dose of 200 mg, once daily (q.d.) given in the evening. 1 cycle is 28 days.

Schedule 2:

Dose escalation was conducted in patients with incurable solid tumors and adequate organ function with sapacitabine b.i.d.×7 consecutive days (days 1-7), seliciclib b.i.d.×3 consecutive days (days 8-10) followed by 11 days of rest. At least 3 patients were evaluated per dose level. Maximum tolerated dose (MTD) was the highest dose level at which less than one-third of at least 6 patients experienced cycle 1 dose limiting toxicity (DLT). Skin biopsies were obtained to assess DNA damage following sapacitabine (day 8 vs pre-treatment) and further augmentation of DNA damage after seliciclib (day 11 vs day 8).

Results 27 patients were treated in accordance with Schedule 2. The MTD and recommended phase II dose (RP2D) is sapacitabine 50 mg b.i.d./seliciclib 1200 mg b.i.d. DLTs were reversible transaminase elevations and neutropenia. The most frequent adverse events (all cycles, regardless of causality) included anorexia, fatigue, abdominal pain, dizziness, nausea, anemia, neutropenia, creatinine elevation, hyperglycemia, hyperbilirubinemia, hypophosphatemia, hypokalemia and hypomagnesemia, the majority mild to moderate in intensity. Skin biopsies showed a 2.3-fold increase in H2AX staining post-sapacitabine (n=16; $P=0.007$) and a further 0.58-fold increase post-seliciclib (n=12; $P=0.069$). Two confirmed partial responses (PRs) occurred in patients with pancreatic and breast cancer, both BRCA mutation carriers. SD as best response $>/=12$ weeks was observed in 6 additional patients, including one BRCA mutation carrier with ovarian cancer (ongoing at 24 weeks).

CONCLUSIONS

Sequential sapacitabine and seliciclib is safe with preliminary antitumor activity. BRCA mutation carrier status may be a potential biomarker for response across multiple tumor types.

Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be covered by the present invention.

The invention claimed is:

1. A method of treating a proliferative disorder in a subject, wherein the proliferative disorder is a solid tumour selected from the group consisting of breast cancer, ovarian cancer, and pancreatic cancer, said method comprising administering to the subject a therapeutically effective amount of (i) sapacitabine, or a metabolite thereof, wherein the metabolite is 1-(-C-Cyano-2-deoxy-β-D-arabino-pentafuranosyl)-cytosine (CNDAC); and (ii) seliciclib; in accordance with a dosing regimen comprising at least one treatment cycle, wherein said treatment cycle comprises:
   (a) administering sapacitabine, or metabolite thereof, twice a day in a dosage of from about 50 to about 300 mg per dose, for 7 consecutive days; and
   (b) administering seliciclib twice a day in a dosage of from about 200 to about 1200 mg per dose for 3 consecutive days;
      followed by a rest period of at least 10 days, or until treatment-related toxicities are resolved, whichever is longer, wherein the seliciclib administered in step (b) is administered after the sapacitabine, or metabolite thereof, in step (a) without a rest period.

2. A method according to claim 1 wherein the seliciclib administration starts the day after the sapacitabine administration has been completed.

3. A method according to claim 1 wherein the treatment cycle is 21 days in length.

4. A method according to claim 1 wherein the treatment cycle comprises:
   (a) administering the sapacitabine, or metabolite thereof, for 7 consecutive days; followed by
   (b) administering the seliciclib for 3 consecutive days; followed by a rest period of 11 days.

5. A method according to claim 1 wherein the treatment cycle is repeated two or more times.

6. A method according to claim 1 wherein the sapacitabine is administered in an amount of about 50 mg twice daily (b.i.d.).

7. A method according to claim 1 wherein the seliciclib is administered in an amount of about 200 mg to about 800 mg per dose.

8. A method according to claim 1 wherein the seliciclib is administered in an amount of about 800 mg twice daily (b.i.d.).

9. A method according to claim 1 wherein the sapacitabine is administered orally.

10. A method according to claim 1 wherein the seliciclib is administered orally or intravenously.

11. A method according to claim 1 wherein the cancer has a BRCA1 and/or a BRCA2 gene mutation.

\* \* \* \* \*